United States Patent [19]
Ito et al.

[11] Patent Number: 5,109,716
[45] Date of Patent: May 5, 1992

[54] APPARATUS AND METHOD FOR MEASURING ADSORPTION/DESORPTION

[75] Inventors: Mutsuhiro Ito; Toshiyasu Abe, both of Miyazaki, Japan; Ryuji Orii, Corvallis, Oreg.; Tomio Yamakoshi, Miyazaki, Japan

[73] Assignee: Fuji-Davison Chemical Ltd., Kasugai, Japan

[21] Appl. No.: 605,958

[22] Filed: Oct. 30, 1990

[30] Foreign Application Priority Data

Feb. 27, 1990 [JP] Japan ................................ 2-46577

[51] Int. Cl.$^5$ .......................................... G01N 15/08
[52] U.S. Cl. ........................................ 73/865.5; 73/38
[58] Field of Search ................................ 73/865.5, 38

[56] References Cited

U.S. PATENT DOCUMENTS

| | | | |
|---|---|---|---|
| 2,729,969 | 1/1956 | Innes ............................. | 73/865.5 X |
| 3,349,625 | 10/1967 | Benusa et al. ................. | 73/865.5 |
| 3,500,675 | 3/1970 | Sandstede et al. ............ | 73/865.5 X |
| 4,489,593 | 12/1984 | Pieters et al. ................. | 73/38 |
| 4,762,010 | 9/1988 | Borghard et al. .............. | 73/865.5 |

*Primary Examiner*—Hezron E. Williams
*Assistant Examiner*—Joseph W. Roskos
*Attorney, Agent, or Firm*—Tarolli, Sundheim & Covell

[57] ABSTRACT

The actual flow rate of gas to the solid-sample container or to the gas reservoir can be precisely obtained according to variances in the pressure of the gas reservoir without directly adjusting the flow rate precisely. The volume of gas not adsorbed in the sample container can be obtained from the pressure in the sample container. The adsorption can easily be determined from the difference between the flow rate of gas and the volume of gas not adsorbed in the sample container. Even if the flow rate fluctuates, the adsorption can precisely be obtained. The desorption can easily be obtained in the same way. Gas is exhausted from the gas reservoir in advance. When desorbed gas in the sample container is continuously exhausted to the gas reservoir, the pressure in the gas reservoir is measured. Since the adsorption and desorption are thus precisely obtained, the adsorption of desorption isotherm can be drawn by plotting the pressure at each point of time and the corresponding adsorption or desorption of the solid sample. Consequently, the surface area, pore diameter distribution, pore volume and the like of the solid sample can precisely be calculated.

17 Claims, 2 Drawing Sheets

APPARATUS AND METHOD FOR MEASURING ADSORPTION/DESORPTION

BACKGROUND OF THE INVENTION

This invention relates to an apparatus and method for measuring adsorption and desorption that precisely measures the volume of gas adsorbed on or desorbed from a solid sample. Specifically, this invention relates to an apparatus for measuring adsorption and desorption to calculate surface area, pore diameter distribution, pore volume and the like of the solid sample. This invention also relates to a method for measuring adsorption and desorption by using the apparatus.

For example, various particles such as solid catalysts, adsorbents, ion-exchangers, and ceramics are widely used as industrial materials. These particles vary in their physical properties such as specific surface area, pore volume and pore diameter distribution according to raw materials and manufacturing conditions. Consequently, the particles vary in industrial performance. When the particles are used as industrial materials, the specific surface area, the pore volume, and the pore diameter distribution of the particles should be precisely known.

Generally, a gaseous-phase adsorption method is used for measuring the physical properties of industrial-material particles. In this method, inert gas such as nitrogen gas is used as adsorbate gas, and a sample physically adsorbs the adsorbate gas. Variances in the pressure and volume of the adsorbate gas are obtained for measuring the adsorption of the sample. In this method, variances with time in adsorption pressure values and adsorbate gas volume at constant temperature are used. The configuration of adsorption isotherm, or hysteresis, seen on the adsorption isotherm between increase and decrease of the adsorption is, therefore, used.

In the related-art method, a batch-process apparatus is used. The batch-process apparatus comprises a measuring portion for measuring volume and pressure of gas and a sample container connected through a valve to the measuring portion. The measuring portion is provided with valves for supplying and exhausting gas to and from the measuring portion, respectively.

When adsorption is measured with the apparatus, a volume M of gas is first introduced into the measuring portion, and the measuring portion is connected to the sample container. When pressure in the measuring portion and the sample container is in equbrium and the adsorption of the sample is in equbrium, a series of processes for measuring pressure values is repeated. At each process, the volume M of gas is increased. The adsorption is calculated from the pressure values, the volume of the measuring portion, and the like. On the other hand, when desorption is measured, the measuring portion is evacuated, and the measuring portion is connected to the sample container. When pressure in the measuring portion and the sample container is in equbrium, a series of processes for measuring values is repeated. At each of the processes, desorbed gas is exhausted from the measuring portion. The desorption is calculated from the pressure values, the volume of the measuring portion, and the like.

However, since time is required until the pressure in the measuring portion and the sample container is in equbrium, the measurement of one sample takes eight to fifteen hours or longer. During the processes, an operator should timely and effectively introduce adsorbate gas into the measuring portion, exhaust desorbed gas from the measuring portion, and open or close the valves. The operator should be experienced in introducing the adsorbate gas and in adjusting the openings of the valves, but his error cannot be avoided to some degree.

A method for measuring adsorption and desorption using a mass flow controller is proposed in Japan Published Unexamined Patent Application No. 61-102538. This method is different from the above method using the batch-process apparatus in that gas is continuously fed little by little into a vacuum sample container with the mass flow controller. The flow rate of gas is substantially kept constant. When gas is continuously supplied to the sample container, adsorption and desorption of gas by a sample are calculated based on the flow rate of gas and measured variances in the pressure of the sample container. Adsorption isotherm is thus obtained. In the method, when gas is introduced into the sample container, the adsorption of the sample in the sample container is kept in equbrium. Pressure values are measured at several points of time from the beginning till the end of the introduction of gas into the sample container. Excessive time is not required for obtaining pressure values. An adsorption isotherm can be obtained in a relatively short period of time.

In the above disclosed method, the adsorption of the sample is calculated in a predetermined equation by using the flow rate of gas. The mass flow controller controls the flow rate of gas substantially constant at a target value. However, the mass flow controller should be frequently adjusted and calibrated so that the flow rate of gas should not deviate from the target value and the adsorption can precisely be calculated. Actually, the flow rate of gas cannot be kept constant, and it sometimes deviates from the target value. Consequently, precise calculation of adsorption or desorption cannot result.

SUMMARY OF THE INVENTION

The object of the present invention is to provide an apparatus and a method for measuring adsorption and desorption that can control the flow rate of gas and precisely obtain an adsorption and desorption isotherm.

To attain this and other objects, the present invention provides an apparatus for measuring adsorption and desorption of gas by a solid sample. The apparatus comprises a sample container with a predetermined volume for introducing the solid sample, a gas reservoir with a predetermined volume for storing gas, a gas exhausting means for exhausting gas from the sample container and the gas reservoir, a gas feeding means for continuously feeding gas from the gas reservoir to the sample container or from the sample container to the gas reservoir, a pressure gauge for measuring pressure in the sample container, and a pressure gauge for measuring pressure in the gas reservoir.

This invention also provides a method for measuring adsorption of the solid sample with the apparatus. The method comprises the steps of: introducing the solid sample into the sample container and concurrently exhausting gas from the sample container with the gas exhausting means; and continuously feeding gas from the gas reservoir kept at predetermined temperature into the sample container kept at predetermined temperature with the gas feeding means. During the step of the feeding of gas, pressure in the sample container and pressure in the gas reservoir are measured with the elapsing of time with the pressure gauges. The flow rate of gas into the sample container is calculated based on the pressure in the gas reservoir and volume of the gas reservoir. The adsorption of the solid sample at each points of time is obtained based on the flow rate, the pressure in the sample container, and the volume of the sample container.

This invention provides a further method for measuring desorption of the solid sample with the apparatus. The second method comprises the steps of: introducing the solid sample into the sample container and concurrently exhausting gas from the gas reservoir with the gas exhausting means; and feeding gas continuously from the sample container kept at predetermined temperature into the gas reservoir kept at predetermined temperature with the gas feeding means. During the step of the feeding of gas, pressure in the sample container and pressure in the gas reservoir are measured with the elapsing of time with respective pressure gauges. The flow rate of gas into the gas reservoir is calculated based on the pressure in the gas reservoir and volume of the gas reservoir. The desorption of the solid sample at each points of time is obtained based on the flow rate, the pressure in the sample container, and the volume of the sample container.

DETAILED DESCRIPTION OF THE PREFERRED EMBODIMENT

Figure 1:
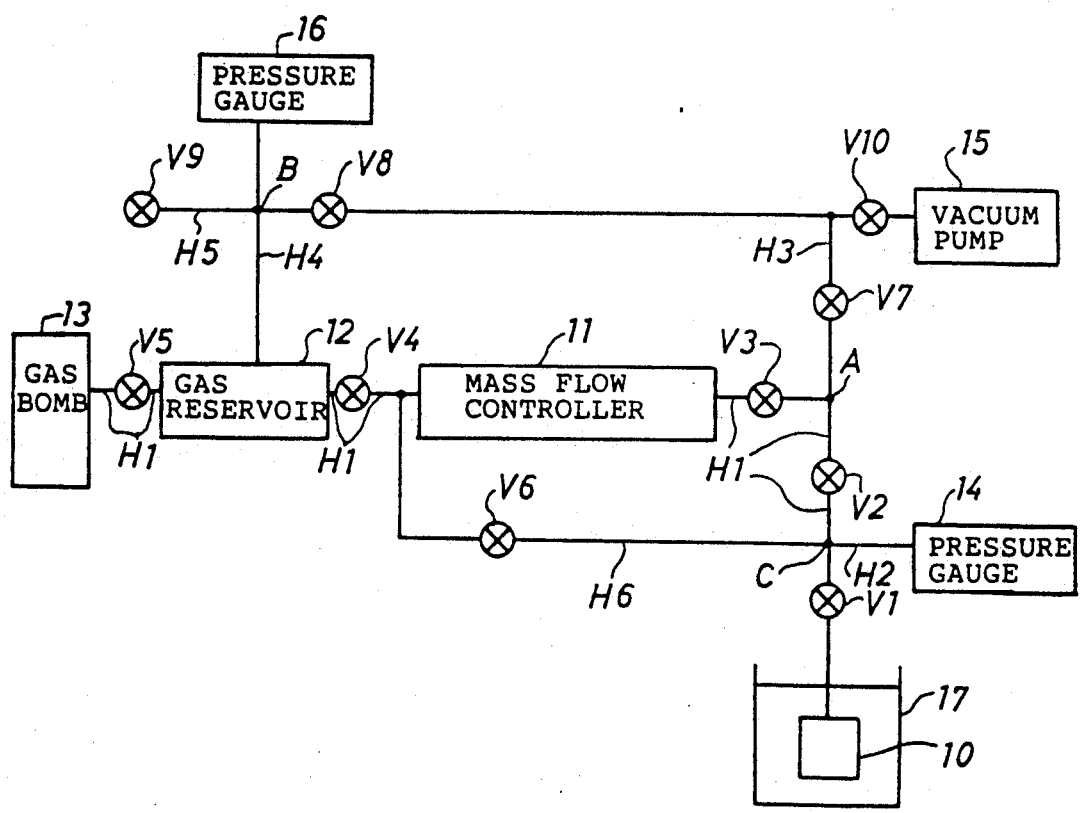
FIG. 1 is a block diagram embodying an apparatus for measuring absorption and desorption of the present invention.

As shown in FIG. 1, the adsorption/desorption measuring apparatus comprises a sample container 10, a mass flow controller 11, a gas reservoir 12, a gas bomb 13, two pressure gauges 14, 16, and a vacuum pump 15. A solid sample is introduced into the sample container 10. In this embodiment, the surface area, the pore diameter distribution, the pore volume and the like of the solid sample are measured. The mass flow controller 11 can continuously supply a specified volume of gas to the sample container 10.

The sample container 10 is connected via piping H1 through the mass flow controller 11 and the gas reservoir 12 to the gas bomb 13.

The pressure gauge 14 and the vacuum pump 15 are, respectively, connected through pipings H2 and H3 to points A and C of the piping H1 connecting the sample container 10 and the mass flow controller 11.

The pressure gauge 16 is connected through a piping H4 to the gas reservoir 12.

One end of a piping H5 opens to the atmosphere, and the other end of the piping H5 goes to the vacuum pump 15. The pipings H4 and H5 intersect at a point B.

At the same time, a piping H6 is laid from a point between the mass flow controller 11 and the gas reservoir 12 to the sample container 10.

Three valves V1, V2, and V3 are provided on the piping H1 between the sample container 10 and the mass flow controller 11. The piping H1 further includes a valve V4 between the mass flow controller 11 and the gas reservoir 12, and a valve V5 between the gas reservoir 12 and the gas bomb 13. A valve V6 is provided on the piping H6 which extends from the point between the mass flow controller 11 and the gas reservoir 12 to the sample container 10. Valves V7 and V10 are provided on the piping H3 between the point A of the piping H1 and the vacuum pump 15, a valve V8 is provided on the piping H5 between the vacuum pump 15 and the intersection B, and a valve V9 is provided at the end of the piping H5 which end opens to the atmosphere.

In this embodiment, as shown in FIG. 1, the sample container 10 is soaked in a refrigerant tank 17, so that the sample container 10 is kept at constant temperature. The liquid level in the refrigerant tank 17 is kept constant, thus preventing the volume in the sample container 10 from changing.

The mass flow controller 11 can be mechanical or electrical. The flow rate of the mass flow controller 11 should be prevented from varying with the fluctuation in the primary and/or the secondary pressure. The operating range of differential pressure between the primary and the secondary sides of the mass flow controller 11 should be wide.

The gas reservoir 12 for storing gas from the gas bomb 13 can be kept constant around room temperature of 25° C. The gas reservoir 12 should contain the predetermined volume at minimum so that the differential pressure of the mass flow controller 11 adjoining the gas reservoir 12 should be kept in the predetermined operating range of the mass flow controller 11. The predetermined volume of the gas reservoir 12 varies with the weight and the pore volume of the sample. For example, when the mass flow rate is 0.5 ml/min.; the weight of the sample is 1 g; the pore volume of the sample is 1 ml/g; the dead volume from the mass flow controller 11 to the sample container 10 is 20 ml; the operating range of the differential pressure of the mass flow controller 11 is between 0.4 kg/cm$^2$A and 3 kg/cm$^2$A; the pressure of the gas reservoir 12 at the start of measurement is 3 kg/cm$^2$A; and nitrogen gas is used, the measurement for this embodiment is executed as follows:

The pressure of the sample container 10, which is equal to the secondary pressure of the mass flow controller 11, should equal atmospheric pressure of about 1 kg/cm$^2$ at the end of the measurement as described later. When the measurement is finished, the residual pressure at the side of the gas reservoir 12 or the primary pressure of the mass flow controller 11 should be 1.4 kg/cm$^2$A at minimum, thereby equaling the minimum differential pressure value of 0.4 kg/cm$^2$A in the operating range, plus the atmospheric pressure of 1 kg/cm$^2$A. By the end of the measurement, the gas reservoir 12 should exhaust about 670 ml of gas (hereinafter referred to as exhaust gas volume) to the sample container 10, so that the pressure of the gas reservoir 12 can reach 1.4 kg/cm$^2$A from 3 kg/cm$^2$A. Consequently, the volume Vol of the gas reservoir 12 should be calculated about 420 ml at minimum based on relationship (3−1.4−)Vol=670 ml.

The volume Vol of the gas reservoir 12 should exceed the calculated value of 420 ml. However, since the flow rate of gas to the sample container 10 is obtained from the variance in the pressure of the gas reservoir 12, too much volume of the gas reservoir 12 adversely affects the precision in reading pressure and in calculating the flow rate of gas. To avoid such adverse influence, a reference value VMIN of the minimum volume of the gas reservoir 12 is calculated in the following equation:

$$VMIN = (Vol_1 + Vol_2)/(P1 - P2).$$

in which

Vol$_1$: gas adsorption of the sample;
Vol$_2$: dead volume of the sample container 10;
P1: the upper limit of the differential pressure in the operating range of the mass flow controller 11; and
P2: the saturation pressure of the sample, plus the lower limit of the differential pressure in the operating range of the mass flow controller 11.

The actual volume of the gas reservoir 12 is set from equal to or ten times, and preferably one and half times to three times, as large as the reference value VMIN.

Calculation of the exhaust gas volume from the gas reservoir 12 will now be explained. Nitrogen adsorbed in pores of the sample is almost in a liquid condition. Nitrogen has a density of 0.808 and a molecular weight of 28. The volume of nitrogen adsorbed in one gram of the sample with a pore volume of 1 ml is 1 ml in a liquid form. When converted into gas, the volume of nitrogen adsorbed in the sample is 646 ml in the following equation:

$$(1 \cdot 0.808)/28 \cdot 22400 = 646 \text{ ml}$$

When the dead volume of 20 ml is added to the calculated volume of 646 ml, the necessary exhaust gas volume is 666 ml, about 670 ml.

The pressure gauge 16 continuously or intermittently measures absolute pressure of the gas reservoir 12. On the other hand, the pressure gauge 14 continuously or intermittently measures the absolute pressure of the sample container 10. As the pressure gauges 14 and 16, semiconductor-type pressure transducers or the like can read the absolute pressure of the gas reservoir 12 and the sample container 10 through computers and record the absolute pressure on recorders.

The vacuum pump 15 exhausts gas from the sample container 10 in preparation for measurement of gas adsorbed in the sample. The pressure gauges 14 and 16 are calibrated in the method described later with the vacuum pump 15, the valves V8, V9 and the like.

The valves V1, V2, V3 and V6 switch the measuring apparatus for this embodiment between the system for measuring the adsorption of the sample and that for measuring the desorption of the sample.

The method for measuring the adsorption of the solid sample with the apparatus for the embodiment will now be explained.

In the preparation for measurement, the pressure gauges 14 and 16 are calibrated, volume of the gas reservoir 12 is measured, and subsequently dead volume of the sample container 10 is measured. Such preparation will now be explained.

1. THE CALIBRATION OF THE PRESSURE GAUGES 14 AND 16

First, the pressure gauges 14 and 16 are calibrated. The valves V1, V3, V4, V5, V6, and V9 are closed, the valves V2, V7, V8, and V10 are opened, and the gas reservoir 12 is evacuated to the maximum, about 0 kg/cm$^2$A, with the vacuum pump 15. The pressure gauges 14 and 16 are adjusted to zero. Subsequently, the vacuum pump 15 is stopped, the valve V9 is opened to the atmosphere, and the readings on the pressure gauges 14 and 16 are adjusted to the atmospheric pressure precisely measured with a mercury barometer, an aneroid barometer or other barometers.

The pressure gauge 14 may be opened to the atmosphere by detaching the sample container 10 before measuring the atmospheric pressure.

2. THE MEASUREMENT OF THE VOLUME $V_o$ OF THE GAS RESERVOIR 12

Volume $V_o$ of the gas reservoir 12 is the sum of the volume of the gas reservoir 12 and that of the piping from the gas reservoir 12 to the mass flow controller 11.

First, a sample container (not shown) with a predetermined volume is connected to the valve V9. Volume Vs of the sample container should be almost the same as that of the gas reservoir 12. The volume of the sample container should be measured at predetermined temperature of 25° C. Subsequently, the valves V4, V8 and V9 are opened, and the valves V5, V6 and V7 are closed. The flow rate of the mass flow controller 11 is set to zero. The sample container as well as the gas reservoir 12 are evacuated with the vacuum pump 15. After the valves V8 and V9 are closed and the valve 5 is opened, nitrogen gas is introduced into the gas reservoir 12. Pressure P0 of the gas reservoir 12 in stable condition is measured with the pressure gauge 16. The valve V9 is then opened, and gas is introduced into the sample container. Pressure P1 on the pressure gauge 16 in stable condition is read. Based on the pressures P0, P1 and the volume Vs of the sample container, the volume $V_o$ of the gas reservoir 12 is calculated in following equations:

$$P0 V_o = P1(V_o + Vs)$$

$$V_o = (P1 Vs)/(P0 - P1)$$

Air should be sufficiently circulated around the gas reservoir 12, the pressure gauge 16, the piping H1 and the like so that temperature should be kept constant.

When the volume $V_o$ of the gas reservoir 12 is measured, the flow through the mass flow controller 11 should be shut off. If the flow cannot be shut off in the structure of the mass flow controller 11, the volume $V_o$ of gas can be measured as follows. First, the sample container 10 with the predetermined volume is connected to the valve V1, and the refrigerant tank 17 is detached. After gas is introduced into the gas reservoir 12 in the same way as aforementioned, the valves V1, V2, V3 and V7 are opened, the valve V6 is kept closed, and the mass flow controller 11 is operated. When the valve V7 is closed, pressures on the pressure gauges 16 and 14 are read as pressures P11 and P21, respectively. After appropriate time period, pressures on the pressure gauges 16 and 14 are read as pressures P12 and P22, respectively. Subsequently, the sample container 10 is detached from the valve V1, and a connection rod with no content is connected to the valve V1. In the same way as aforementioned, variances in the pressures are obtained with the pressure gauges 16 and 14. Specifically, the initial pressures of the pressure gauges 16 and 14 are read as P13 and P23, respectively, and the pressures after appropriate time period are read as P14 and P24, respectively.

When dead volume of the line enclosed by the mass flow controller 11 and the valves V1, V6 and V7 is Vt, following two equations (1) and (2) are obtained:

$$P11 V_o - P12 V_o = P22(Vt + Vs) - P21(Vt + Vs)$$

$$(P11 - P12)/(P22 - P21) = (Vt + Vs)/V_o \quad (1)$$

$$P13 V_o - P14 V_o = P24 Vt - P23 Vt$$

$$(P13 - P14)/(P24 - P23) = Vt/V_o \quad (2)$$

When Vt is deleted from equations (1) and (2), $V_o$ is obtained as follows:

$$V_o = V_s / [(P11 - P12/P22 - P12) - (P13 - P14/P24 - P23)]$$

By repeating the above procedure several times, the volume $V_o$ is precisely obtained.

3. THE MEASUREMENT OF THE DEAD VOLUME Vt

After connecting the sample container 10 to the valve V1, the sample container 10 is soaked in the refrigerant tank 17. Subsequently, in the same way as mentioned in above preparation 2, pressures P31, P32, P41 and P42 corresponding to the pressures P11, P12, P21, P22, respectively, are obtained. Based on these pressures and the obtained values of Vs and $V_o$, the dead volume Vt in standard condition is obtained from equation (1). After obtaining pressures P33, P34, P43 and P44 corresponding to the pressures P13, P14, P23, P24, respectively, the dead volume Vt can be obtained from equation (2).

After the above preparations are finished, adsorption of the solid sample is measured.

First, the specified sample is inserted in the sample container 10, and gas is introduced and stored in the gas reservoir 12 in the same way as mentioned in above preparation 3. Subsequently, gas is run from the gas reservoir 12 through the mass flow controller 11 in operation condition to the sample container 10. As time elapses after gas begins to flow, pressures of the gas reservoir 12 and the sample container 10 are measured with the pressure gauges 16 and 14, respectively.

Variances with time in the pressures of the gas reservoir 12 and the sample container 10 are continuously and automatically recorded on the recorder with a microcomputer connected to the pressure gauges 16 and 14.

Total dead volume Vtt, which is the sum of the dead volume Vt and the dead volume $Vol_2$ of the sample container 10, varies with the volume of the sample under measurement. To avoid error in measurement, after introducing the sample into the sample container 10, the dead volume Vt can be measured by using gas which is not adsorbed into the sample, such as helium gas and the like. The dead volume Vt can be calculated from the refrigerant temperature and the true specific gravity of the sample. Other appropriate methods may be used.

Based on the obtained pressure value of the gas reservoir 12, the mass Qc of gas exhausted from the gas reservoir 12 to the sample container 10 is precisely calculated at a given time t. Based on the mass Qc and the pressure value of the sample container 10 measured with the pressure gauge 14, adsorption Qs of the sample is calculated.

The mass Qc is calculated in following equation:

$$Qc\ [mol] = (Ps - Pt1)V_o/RT1,$$

in which

Ps [mmHg]: pressure when the gas reservoir 12 starts exhausting gas;

Pt1 [mmHg]: pressure of the gas reservoir 12 at the given time t;

$V_o$ [ml]: volume of the gas reservoir 12; and

T1 [K]: temperature in the gas reservoir 12, which is almost constant.

The adsorption Qs is calculated in following equation:

$$Qs\ [mol/g] = [Qc - (Pt2 Vtt/RT2)]/W,$$

in which

Pt2 [mmHg]: pressure of the sample container 10 measured at the time t;

Vtt [ml]: total dead volume;

T2 [K]: temperature converted when the dead volume Vt is measured;

R: constant of gas; and

W [g]: weight of the sample.

Figure 2:
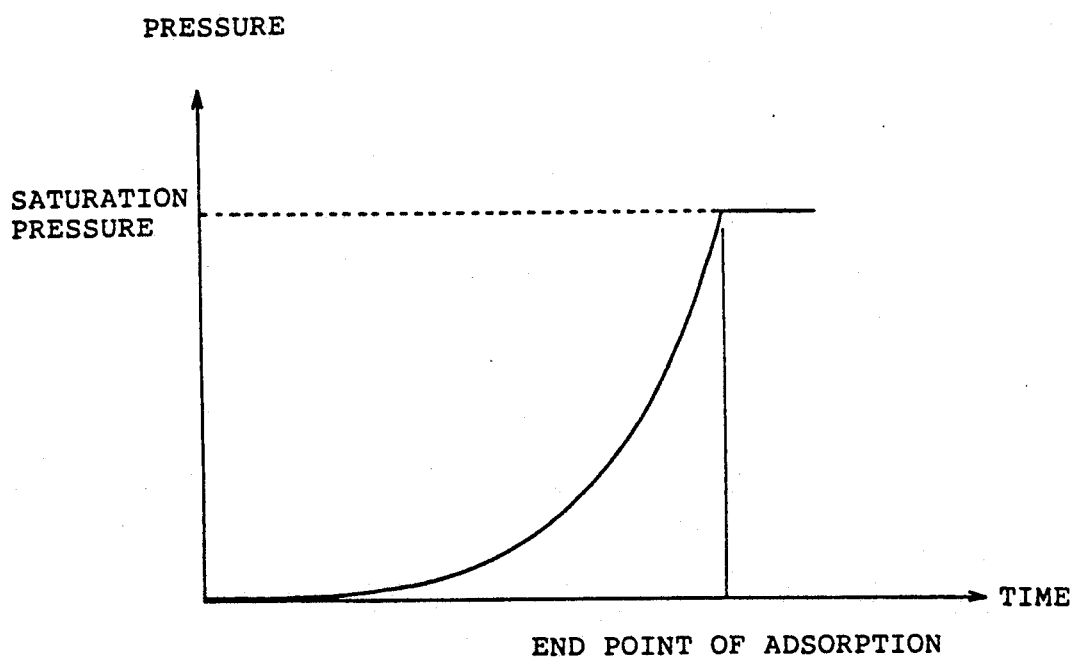
FIG. 2 is a graph showing variances in pressure with time during measurement of adsorption.

The graph in FIG. 2 shows the pressure values measured as time passes. The end-point value of the adsorption can be clearly identified by intersecting the extension line of saturation pressure with the rising curve of the adsorption in FIG. 2.

Since the flow rate of gas exhausted to the sample container 10 at each points of time is thus precisely obtained with the pressure gauge 16, the adsorption of the sample at each points of time can be precisely calculated. A precise adsorption isotherm results.

With the apparatus for this embodiment, desorption of the sample can also be calculated. The measurement of desorption with the apparatus after the measurement of the adsorption will now be explained.

After measuring the adsorption of the sample, the valves V8 and V10 are opened, the valves V7, V4, V5 and V9 are kept closed, and the gas reservoir 12 is evacuated with the vacuum pump 15. Subsequently, the valves V7, V3, V6 and V1 are opened, the valves V4 and V2 are closed, the mass flow controller 11 is operated, and values on the pressure gauges 4 and 16 are recorded.

Subsequently, by closing the valve V10, desorption is started. Since pressure is saturated, the pressure gauge 14 indicates constant pressure with no decrease for some time after the desorption starts. When the pressure gauge 14 starts indicating decrease of the pressure, the desorption isotherm starts extending. Desorption mass Qd of gas flowing from the sample container 10 as well as actual desorption Qt from the sample are calculated from the increase in the pressure of the gas reservoir 12 indicated by the pressure gauge 16 as follows:

$$Qd = (Ppt_1 - Pps)Vol_3/RT_1$$

$$Qt = [Qd - (Ppt_2 Vtt/RT_2)]/W,$$

in which $Ppt_1$ [mmHg]: pressure of the gas reservoir 12 measured at time $t_1$;

Pps [mmHg]: pressure of the gas reservoir 12 at the start of measurement;

$Vol_3$ [ml]: volume of the gas reservoir 12 at the time of desorption;

$T_1$ [K]: temperature of the gas reservoir 12, which is almost constant;

$Ppt_2$ [mmHg]: pressure of the sample container 10 at time $t_2$;

Vtt [ml]: total dead volume $T_2$ [K]: temperature converted when the dead volume Vt is measured;

R: constant of gas; and

W [g]: weight of the sample.

The desorption isotherm is obtained by plotting the value $Ppt_2$ of the pressure gauge 14 at time $t_1$ and value $Q_{so}-Q_t$ obtained by subtracting the desorption $Q_t$ at time $t_1$ from desorption $Q_{so}$ at the saturation pressure.

When the pressure in the gas reservoir 12 approximates the pressure in the sample container 10 during the measurement of the desorption, gas fails to flow through. If gas cannot flow through, the valve V3 is closed, the valve V10 is opened, and the gas reservoir 12 is again evacuated with the vacuum pump 15. By opening the valve V3 and closing the valve V10, the measurement of the desorption can be restarted. The desorption isotherm can thus be obtained in all the ranges of pressures.

In the same way as that for the volume $V_o$, the volume $Vol_3$ of the gas reservoir 12 at the time of desorption is calculated from variances in pressure when the sample container with the known volume and a glass rod with no volume are attached to the valve V1 and are thus connected through the mass flow controller 11 to the gas reservoir 12.

EXAMPLES OF ACTUAL MEASUREMENT

Actual measurement was carried out as follows.

Silica gel was used as the sample, and nitrogen gas was used as adsorbate. The mass flow rate indicated by the mass flow controller 11 was adjusted to 2.50 SCCM prior to the measurement. The actual mass flow rate was calculated between 2.23 SCCM and 2.25 SCCM based on the drop in the pressure of the gas reservoir 12. Based on the calculated mass flow rate, the specific surface area and the pore volume of the sample were calculated. The specific surface area of the sample was calculated based on the B.E.T. adsorption isotherm. On the other hand, the pore volume of the sample was obtained from the adsorption corresponding to the relative pressure of 1.0(P/P00).

| Measurement No. | Specific Surface Area ($m^2/g$) | Pore Volume (ml/g) |
| --- | --- | --- |
| 1 | 697 | 0.393 |
| 2 | 692 | 0.389 |
| 3 | 699 | 0.394 |
| 4 | 689 | 0.386 |
| 5 | 685 | 0.383 |

As shown in the above, the specific surface area of the sample was between 685 $m^2/g$ and 699 $m^2/g$, and the pore volume of the sample was between 0.394 ml/g and 0.383 ml/g. Stable measurement was thus realized. The mass flow controller 11 was adjusted only once at the initial stage of the measurement.

Comparison data will now be explained.

The value indicated by the mass flow controller 11 was kept constant at 0.50 SCCM. The gas reservoir 12 was detached from the apparatus. With the same sample and in the same conditions as those in the above measurement, the comparison data was obtained.

| Measurement No. | Specific Surface Area ($m^2/g$) | Pore Volume (%) |
| --- | --- | --- |
| 1 | 684 | 0.383 |
| 2 | 672 | 0.382 |
| 3 | 668 | 0.376 |
| 4 | 675 | 0.377 |
| 5 | 652 | 0.371 |
| 6 | 648 | 0.345 |
| 7 | 656 | 0.361 |
| 8 | 736 | 0.452 |
| 9 | 633 | 0.364 |
| 10 | 655 | 0.382 |

As shown in the above, the specific surface area of the sample varied widely between 633 $m^2/g$ and 736 $m^2/g$. The pore volume of the sample also varied widely between 0.345 ml/g and 0.452 ml/g. The mass flow controller 11 had to be adjusted several times.

The known gaseous phase adsorption method using nitrogen gas resulted as follows:

the specific surface area: 706.3±4.6 $m^2/g$ the pore volume: 0.40 ml/g

The invention is not limited to the embodiment illustrated and described. Other various embodiments within the scope of the invention are possible.

What is claimed is:

1. An apparatus for measuring adsorption and desorption of a gas by a solid sample, comprising:

sample containing means having a predetermined volume $Vol_2$ for containing the solid sample and gas;

gas containing means having a predetermined volume Vo for containing gas;

exhaust means for selectively exhausting gas from either the sample containing means or the gas containing means;

gas feeding means for selectively continuously feeding gas at a flow rate either from the gas containing means to the sample containing means or form the sample containing means to the gas containing means;

first pressure measuring means for measuring the pressure of the gas in the gas controlling means; and second pressure measuring means for measuring the pressure of the gas in the sample containing means;

the absorption and desorption being calculated based on the flow rate of gas between the gas containing means and the sample containing means, the pressure measured by the second pressure measuring means and the volume $Vol_2$ of the sample containing means, the adsorption of the solid sample being calculated while the gas feeding means feeds gas from the gas containing means to the sample containing means based on the flow rate of gas from the gas containing means into the sample containing means.

2. The apparatus of claim 1, in which:

the flow rate of gas from the gas containing means into the sample containing means is calculated by determining the mass Qc of gas fed by the gas feeding means from the gas containing means into the sample containing means over time; wherein the mass Qc of gas fed from the gas containing means to the sample containing means is calculated according to the following equation:

$$Qc = (Ps - Pt1)Vo/RT1$$

where Ps is the pressure in the gas containing means when the gas feeding means begins to feed gas from the gas containing means into the sample containing means, Pt1 is the pressure in the gas containing means at a given time t, T1 is the temperature in the gas containing means, and R is a constant.

3. The apparatus of claim 2, in which the adsorption of the solid sample Qs is calculated according to the following equation:

$$Qs = [Qc - (Pt2\, Vtt/RT2)]/W$$

where Pt2 is the pressure in the sample containing means at a given time t, Vtt is the sum of the volume $Vol_2$ of the sample containing means and a dead volume Vt in the system, T2 is the temperature of the system at the time dead volume Vt is measured, and W is the weight of the sample.

4. The apparatus of claim 3, further comprising isotherm calculation means for calculating an adsorption isotherm from the adsorption calculated at successive points in time.

5. The apparatus of claim 1, in which the desorption of the solid sample is calculated after the calculation of adsorption while the gas feeding means feeds gas from the sample containing means to the gas containing means based on the flow rate of gas from the sample containing means into the gas containing means.

6. The apparatus of claim 5, in which:

the flow rate of gas from the gas containing means into the sample containing means is calculated by determining the mass Qd of gas fed by the gas feeding means from the sample containing means into the gas containing means over time; wherein the mass Qd of gas fed from the sample containing means to the gas containing means is calculated according to the following equation:

$$Qd = (Ppt1 - Pps)Vol_3/RT1$$

where Ppt1 is the pressure in the gas containing means measured at time t1, Pps is the pressure in the gas containing means at the start of measurement, $Vol_3$ is the volume of the gas containing means at the time of desorption, T1 is the temperature of the gas containing means, and R is a constant.

7. The apparatus of claim 6, in which the adsorption of the solid sample Qt is calculated according to the following equation:

$$Qt = [Qd - (Ppt2\, Vtt/RT2)]/W$$

where Ppt2 is the pressure in the sample containing means at a given time t2, Vtt is the sum of the volume $Vol_2$ of the sample containing means and a dead volume Vt in the system, T2 is the temperature of the system at the time dead volume Vt is measured, and W is the weight of the sample.

8. The apparatus of claim 7, further comprising isotherm calculation means for calculating a desorption isotherm from the adsorption calculated at successive points in time.

9. A method of measuring adsorption of gas from a solid sample, comprising the steps of:

introducing the solid sample into a sample container having a predetermined volume while concurrently exhausting gas from the sample container;

continuously feeding gas from a gas reservoir having a predetermined volume into the sample container, the gas in the gas reservoir being kept at a predetermined temperature;

measuring the pressures in the sample container and the gas reservoir while the gas is continuously fed from the gas reservoir into the sample container;

calculating a flow rate of the gas into the sample container based on the pressure in and volume of the gas reservoir; and obtaining the adsorption of the solid sample based on the flow rate, the pressure in the sample container, and the volume of the sample container.

10. A method of measuring adsorption of gas from a solid sample, comprising the steps of:

introducing the solid sample into a sample container having a predetermined volume while concurrently exhausting gas from the sample container;

continuously feeding gas from a gas reservoir having a predetermined volume into the sample container, the gas in the gas reservoir being kept at a predetermined temperature;

measuring the pressure in the sample container and the gas reservoir while the gas is continuously fed from the gas reservoir into the sample container;

calculating a flow rate of the gas into the sample container based on the pressure in and volume of the gas reservoir; and obtaining the adsorption of the solid sample based on the flow rate, the pressure in the sample container, and the volume of the sample container;

the flow rate of gas from the gas containing means into the sample containing means being calculated by determining the mass Qc of gas fed by the gas feeding means from the gas containing means into the sample containing means over time; wherein the mass Qc of gas fed from the gas containing means to the sample containing means is calculated according to the following equation:

$$QC = \frac{(Ps - Pt1)Vo}{RT1}$$

where Ps is the pressure in the gas containing means when the gas feeding means begins to feed gas from the gas containing means into the sample containing means, Pt1 is the pressure in the gas containing means at a given time t, T1 is the temperature in the gas containing means and R is a constant.

11. The apparatus of claim 10, in which the adsorption of the solid sample Qs is obtained by using the following equation:

$$Qs = [Qc - (Pt2\, Vtt/RT2)]/W$$

where Pt2 is the pressure in the sample containing means at a given time t, Vtt is the sum of the volume $Vol_2$ of the sample containing means and a dead volume Vt in the system, T2 is the temperature of the system at the time dead volume Vt is measured, and W is the weight of the sample.

12. The apparatus of claim 11, further comprising the step of calculating an adsorption isotherm from the adsorption calculated at successive points in time.

13. A method of measuring desorption of gas from a solid sample, comprising the steps of:

introducing the solid sample into a sample container having a predetermined volume while concurrently exhausting gas from a gas container having a predetermined volume;

continuously feeding gas from the sample container into the gas container, the gas in the sample container being kept at a predetermined temperature;

measuring the pressures in the sample container and the gas reservoir while the gas is continuously fed from the sample container into the gas reservoir;

calculating a flow rate of the gas into the gas reservoir based on the pressure in and volume of the gas reservoir; and obtaining the desorption of the solid sample based on the flow rate, the pressure in the sample container, and the volume of the sample container.

14. A method of measuring desorption of gas from a solid sample, comprising the steps of:

introducing the solid sample into a sample container having a predetermined volume while concurrently exhausting gas from a gas container having a predetermined volume;

continuously feeding gas from the sample container into the gas container, the gas in the sample container being kept at a predetermined temperature;

measuring the pressures in the sample container and the gas reservoir while the gas is continuously fed from the sample container into the gas reservoir;

calculating a flow rate of the gas into the gas reservoir based on the pressure in and volume of the gas reservoir; and obtaining the adsorption of the solid sample based on the flow rate, the pressure in the sample container and the volume of the sample container;

the flow rate of gas from the gas containing means into the sample containing means being calculated by determining the mass Qd of gas fed by the gas feeding means from the sample containing means into the gas containing means over time; wherein the mass Qd of gas fed from the sample containing means to the gas containing means is calculated according to the following equation:

$$Qd = \frac{(Ppt1 - Pps)Vol_3}{RT1}$$

where Pptl is the pressure in the gas containing means measured at time t1, Pps is the pressure in the gas containing means at the start of measurement, $Vol_3$ is the volume of the gas containing means at the time of desorption, T1 is the temperature of the gas containing means, and R is a constant.

15. The apparatus of claim 14, in which the adsorption of the solid sample Qt is obtained by using the following equation:

$$Qt = [Qd - (Ppt2Vtt/RT2)]/W$$

where Ppt2 is the pressure in the sample containing means at a given time t2, Vtt is the sum of the volume $Vol_2$ of the sample containing means and a dead volume Vt in the system, T2 is the temperature of the system at the time dead volume Vt is measured, and W is the weight of the sample.

16. The apparatus of claim 15, further comprising the step of calculating a desorption isotherm from the adsorption calculated at successive points in time.

17. An apparatus for measuring adsorption and desorption of a gas by a solid sample, comprising:

sample containing means having a predetermined volume $Vol_2$ for containing the solid sample and gas;

gas containing means having a predetermined volume Vo for containing gas;

exhaust means for selectively exhausting gas from either the sample containing means or the gas containing means;

gas feeding means for selectively continuously feeding gas at a flow rate either from the gas containing means to the sample containing means or from the sample containing means to the gas containing means;

first pressure measuring means for measuring the pressure of the gas in the gas containing means; and second pressure measuring means for measuring the pressure of the gas in the sample containing means;

the absorption and desorption being calculated based on the flow rate of gas between the gas containing means and the sample containing means, the pressure measured by the second pressure measuring means and the volume $Vol_2$ of the sample containing means.

* * * * *

UNITED STATES PATENT AND TRADEMARK OFFICE
CERTIFICATE OF CORRECTION

PATENT NO. : 5,109,716

DATED : May 5, 1992

INVENTOR(S) : Mutsuhiro Ito, Toshiyasu Abe, Ryuji Orii, Tomio Yamakoshi

It is certified that error appears in the above-identified patent and that said Letters Patent is hereby corrected as shown below:

Column 10, Line 34, Claim 1, change "form" to --from--.

Column 10, Line 38, Claim 1, change "controlling" to --containing--.

Signed and Sealed this

Seventeenth Day of August, 1993

Attest:

BRUCE LEHMAN

Attesting Officer    Commissioner of Patents and Trademarks